United States Patent [19]

Morrow

[11] 4,254,124

[45] Mar. 3, 1981

[54] ANTIDEPRESSANT AGENT

[75] Inventor: Duane F. Morrow, Evansville, Ind.

[73] Assignee: Mead Johnson & Company, Evansville, Ind.

[21] Appl. No.: 78,536

[22] Filed: Sep. 24, 1979

[51] Int. Cl.$^3$ ............... C07D 401/14; A61K 31/495; A61K 31/41

[52] U.S. Cl. ..................................... 424/250; 544/362

[58] Field of Search ........................ 544/362; 424/250

[56] References Cited

U.S. PATENT DOCUMENTS 3,381,009   4/1968   Palazzo et al. ..................... 544/362

OTHER PUBLICATIONS

Silvestrini et al. Int J. Neuropharmacol 7, pp. 587–599, (1968).
Fabre et al. Current Therapeutic Research 25 (6), pp. 827–834 (1979).

*Primary Examiner*—Jose Tovar
*Attorney, Agent, or Firm*—R. E. Carnahan; R. H. Uloth

[57] ABSTRACT

2-[3-[4-[3-(Trifluoromethyl)phenyl]-1-piperazinyl]-propyl]-1,2,4-triazolo[4,3-a]pyridin-3(2H)-one and its pharmaceutically acceptable acid addition salts are antidepressant agents.

6 Claims, No Drawings

ANTIDEPRESSANT AGENT

FIELD OF THE INVENTION

The heterocyclic carbon compounds with which the present invention is concerned are piperazines having an additional pyridine ring which is part of a bicyclo ring system (Class 544, subclass 362). It is also concerned with drug bio-affecting and body-treating processes employing these compounds and their salts (Class 424, subclass 250).

DESCRIPTION OF THE PRIOR ART

U.S. Pat. No. 3,381,009 patented Apr. 30, 1968 refers to 2-[3-[4-arylpiperazin-1-yl]propyl]-1,2,4-triazolo[4,3-a]pyridin-3(2H)-ones in which the aryl group is phenyl or substituted phenyl. The compound with which the present invention is concerned is a member of this series in which the substituent is trifluoromethyl. The patent makes no reference to a trifluoromethyl substituted compound. The compound preferred by the prior art is 2-[3-[4-(3-chlorophenyl)-1-piperazinyl]propyl]-1,2,4-triazolo[4,3-a]pyridin-3(2H)-one which is known by the name trazodone, and has also been referred to as AF 1161. Pharmacological data summarized in the foregoing patent reveal that trazodone exhibits tranquilizing action, hypotensive action, and analgesic action in various animal tests. The data resemble that of the major tranquilizers or anti-psychotic agents such as chlorpromazine more than the minor tranquilizers or anxiolytic agents such as meprobamate and diazepoxide.

The pharmacological properties of trazodone have been described in more detail by Silvestrini, et al. in International Journal of Neuropharmacology, 7, 587–599 (1968). In clinical use the compound has proven to be an antidepressant equivalent in effectiveness to imipramine but with fewer side effects (Fabre, et al., Current Therapeutic Research, 25, 827–834 (1979)).

SUMMARY OF THE INVENTION

The compounds with which the present invention is concerned have the following structural formula in which the ring positions have been numbered for nomenclature purposes.

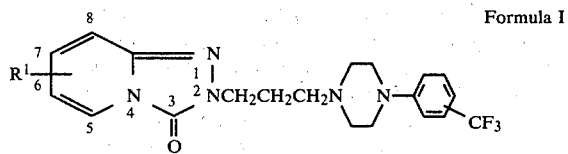

Formula I

In Formula I, $R^1$ is hydrogen or lower alkyl located in the 5, 6, 7, or 8 position of the 1,2,4-triazolo[4,3-a]pyridin-3(2H)-one ring. The trifluoromethyl group ($CF_3$) is located in the 2, 3, or 4 position of the phenyl ring. The invention includes the pharmaceutically acceptable acid addition salts of the foregoing substances and their use in the treatment of depressive disorders including endogenous depression, neurotic depression, or depression accompanying a psychosis.

The pharmaceutically acceptable acid addition salts are those in which the anion does not contribute significantly to the toxicity or pharmacological activity of the salt and, as such, they are the pharmacological equivalents of the bases of Formula I. They are preferred for medical usage. In some instances, they have physical properties which make them more desirable for pharmaceutical formulation purposes such as solubility, lack of hygroscopicity, compressibility with respect to tablet formation and compatibility with other ingredients with which the substance may be used for pharmaceutical purposes. The salts are made by reaction of the base of Formula I with the selected acid preferably by contact in solution. They may also be made by metathesis or treatment with an ion exchange resin under conditions in which the anion of one salt of the substance of the Formula I is replaced by the anion of another under conditions which allow for separation of the undesired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, benzoic, phosphoric, nitric, mucic, isethionic, glucosaccharic, palmitic, heptanoic, and others.

The preferred compound of Formula I is 2-[3-[4-[3-(trifluoromethyl)phenyl]-1-piperazinyl]pyropyl]-1,2,4-triazolo[4,3-a]pyridin-3(2H)-one referred to for convenience as MJ 12762. In animal tests MJ 12762 is comparable in antidepressant activity to trazodone. Other animal tests indicate a significantly reduced propensity for adverse reactions with regard to central nervous system depression, hypotensive action, and others. Its acute toxicity in the mouse appears to be somewhat greater than that of trazodone but again the propensity for signs of overt pharmacologic activity unrelated to its utility is reduced as compared to trazodone. Accordingly, MJ 12762 and the other compounds of this invention may be administered in dosage forms of a similar type and size as trazodone. Oral or parenteral treatment with from about 150 to 500 mg. per day in the treatment of depression is indicated for the substances of Formula I.

DETAILED DESCRIPTION OF THE INVENTION

When reserpine is injected intravenously into a mouse at a dose of 2.0 mg./kg., ptosis occurs. However, if the mouse is treated orally with one of the clinically effective antidepressant drugs such as imipramine or trazodone before the reserpine is injected, ptosis is prevented (Niemegeers, Industrial Pharmacology, Vol. 2—Antidepressants, Ed. by S. Fielding and H. Lal, pp. 73–98, Futura, New York, N.Y. 1975). For example, an oral dose of imipramine of 6.5 mg./kg. or of trazodone of 36 mg./kg. will prevent reserpine from having this effect when administered subsequently in 50% of the animals ($ED_{50}$). MJ 12762 exhibits $ED_{50}$ 14 mg./kg. (p.o.) and, accordingly, is two to three times more potent than trazodone.

Adverse reactions sometimes observed in the treatment of patients suffering from endogenous or neurotic depression with trazodone include hypotension, fatigue, drowsiness, and nasal or sinus congestion. Animal tests with MJ 12762 which suggest a reduced propensity for these adverse reactions to occur include measurement of spontaneous motor activity in the mouse and observation of cardiovascular, somatic, and visceral effects in the anesthetized dog. More particularly, in the measurement of spontaneous motor activity in the mouse using the device and method described by Kissel in U.S. Pat. No. 3,100,473 patented Aug. 13, 1963, MJ 12762 caused neither stimulation nor depression when administered to groups of mice at doses of 20, 40 and 80 mg. per kg. orally. In contrast, trazodone at a dose of 15.3 mg./kg. caused a 30% reduction in spontaneous motor activity. In the dog anesthetized with pentobarbitol sodium and arranged for the recording of carotid arterial blood pressure, MJ 12762 was without effect on blood pressure at intravenous doses of 1 mg. and 10 mg./kg. intravenously. A lack of alpha-adrenergic blocking action was indicated by failure of this substance to effect the blood pressure response to 1-epinephrine. In contrast, trazodone exerted a depressor response at doses of both 1 and 10 mg./kg. intravenously and blocked the effect of 1-epinephrine bitartrate at a dose of 10 mg./kg. intravenously signifying alpha-adrenergic blocking action. Other animal test results in which MJ 12762 has been compared to trazodone are arranged in the following table.

| Test | ORAL DOSES (mg./kg.) | |
|---|---|---|
| | MJ 12762 | Trazodone |
| Mouse, tail clip (analgetic)[1] | $ED_{50} = 94$ | $ED_{50} = 55.5$ |
| Reduction of phenylquinone writhing in mice (analgetic)[2] | $ED_{50} = 6.1$ | $ED_{50} = 21.8$ |
| Inhibition of pernicious preening in mice (anti-psychotic or analgetic)[3] | Inactive (2 of 10 animals responded at 31) | $ED_{50} = 43$ |
| $ALD_{50}/ATD_{50}$ Mouse[4] | 250–500/ 8–15.7 | 940/2–4 |

[1]Bianchi, et al., Brit. J. of Pharmacology 9, 280 (1954).
[2]Hendershot, et al., J. Pharmacol. & Exptl. Ther. 125, 237 (1959).
[3]Wilfon, et al., Federation Proceedings 19, 21 (1960).
[4]Groups of 10 mice treated variously with geometrically increasing doses of test compound with observations of lethal toxicity ($ALD_{50}$) and for first signs of pharmacologic activity ($ATD_{50}$).

Trazodone and MJ 12762 were similar in their effects on the electroencephalogram of the cat recorded from areas of the cortex, amigdulla, and hippocampus.

The compounds of the present invention are prepared from starting materials of Formulas II and III and the dihalide of the formula $XCH_2CH_2CH_2X'$ where X and X' are independently selected from chlorine, bromine, and iodine. Preferably at least one of X and X' is bromine or iodine.

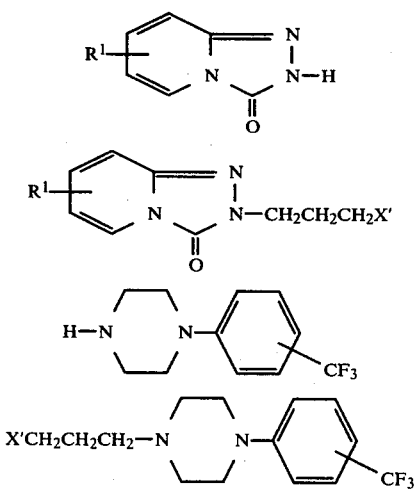

(II)

(IV)

(III)

(V)

A sequential process is involved in which the starting material of either Formula II or Formula III is caused to react with the dihalide and the resulting intermediate is then caused to react with the other starting material. For instance, the dihalide may be first condensed with the starting material of Formula III and the resulting intermediate then caused to react with the starting material of Formula II. One or the other of the intermediates shown in Formulas IV and V is involved, Formula IV being obtained from Formula II by condensation of the latter with the dihalide, and Formula V being obtained from Formula III by condensation of the latter with the dihalide.

In the sequence starting with Formula II the latter is first converted to the sodium or potassium salt by dissolving in warm aqueous sodium or potassium hydroxide and allowing the salt to crystallize from the solution on cooling. The hydrogen atom in the 2-position of Formula II is the acidic functional group which forms the salt. The condensation of the sodium or potassium salt of the starting material of Formula II with the dihalide of the Formula $XCH_2CH_2Ch_2X'$ or with the intermediate of Formula V is carried out by heating the two reactants at a temperature in the range of 80°–150° C. in equimolecular quantities in a liquid reaction medium which is inert under the reaction conditions. Preferably, a reaction medium is chosen which has a boiling point within the foregoing temperature range and refluxing of the reaction mixture is employed for temperature control during a reaction period of 2 to 24 hours. Suitable reaction inert liquid media include the liquid hydrocarbons, hydrocarbon nitriles, and hydrocarbon ethers such as xylene, acetonitrile, and dibutylether.

For preparation of the intermediate of Formula V by reaction of the starting material of III with the indicated dihalide, the two reactants are contacted in a reaction inert liquid medium at room temperature for from 2 to 18 hours in the presence of a strong base such as sodium hydroxide or potassium hydroxide when using a reaction medium containing water, or with a sodium or potassium alkoxide, hydride, oxide, or amide when using a liquid medium which is nonreactive to these bases. A mixture of equal volumes in water and acetone is a convenient and preferred reaction medium with sodium hydroxide as the base.

Starting materials of Formula III and the dihalides are articles of commerce or can be prepared by known methods. The triazolopyridinones of Formula II have been described in the literature or can be conveniently prepared by the reaction of 2-chloro-$R^1$-pyridine with semicarbazide. The preferred sequence is to treat the sodium or potassium salt of Formula II with the intermediate of Formula V which is prepared in a preliminary step from the dihalide and the starting material of Formula III. This is illustrated in Procedures 2 and 4 below. Improved yields are obtained according to this sequence relative the sequence involving first preparation of the intermediate of Formula IV.

DESCRIPTION OF SPECIFIC EMBODIMENTS

In the following procedures temperatures are expressed in degrees Centigrade. Melting points are corrected values according to the USP method where indicated (corr.). The nuclear magnetic resonance (NMR) spectral characteristics refer to chemical shifts (δ) downfield expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), multiplet (m), doublet (d), triplet (t), or quadruplet (q) with coupling constant reported where appropriate. The format is NMR (solvent): δ(relative area, multiplicity, J value, and, in some instances, indicated structural characteristics). Abbreviations employed are DMSO-d$_6$ (deuterodimethylsulfoxide), IR (infrared), KBr (potassium bromide), and d (decomposition). Others are common and have well established meanings. The infrared spectra described include only absorption wavelengths (cm$^{-1}$) having functional group identification value. Unless indicated otherwise, KBr was employed as diluent for IR spectral determinations.

Procedure 1. 1,2,4-Triazolo[4,3-a]pyridin-3(2H)-one

A mixture of 50 g. (0.44 mole) of 2-chloropyridine and 98.22 g. (0.88 mole) of semicarbazide hydrochloride in 150 ml. of 2-ethoxyethanol was heated to reflux and then treated with a solution of 1 ml. of concentrated sulfuric acid (36 N) in 5 ml. of 2-ethoxyethanol. The resulting solution was refluxed for 18 hr., cooled to about 60°, and treated with 150 ml. of water. The mixture was stirred, cooled to 0°, and kept 0.5 hr. and the solid was collected on a filter. The solid was washed well with water and dried under reduced pressure, to give 35.0 g (59%) of product, m.p. 230°–231°, which was sufficiently pure to be used for the next step.

Anal. Found: C, 52.96; H, 3.75; N, 30.94.

Procedure 2.
5-Methyl-1,2,4-triazolo[4,3-a]pyridin-3(2H)-one

The method of Procedure 1 was repeated using 2-chloro-6-methylpyridine as starting material. The product was obtained in 33% yield, m.p. 182°–183°.

Anal. Found: C, 56.42; H, 4.80; N, 28.30.

Procedure 3. Sodium 1,2,4-Triazolo[4,3-a]pyridin-3(2H)-one

The triazole from Procedure 1 (41.2 g., 0.31 mole) was dissolved in a solution of 12.19 g. (0.31 mole) of NaOH in 230 ml. of water at 80°. The solution was then chilled at 5° and left overnight. The resulting precipitate was collected on a filter and dried under reduced pressure, to afford 36.0 g. (75%) of light yellow salt, m.p. 320°. Concentration of the mother liquors afforded an additional 8.3 g. (17%) of salt. The triazole of Procedure 2 was converted to the sodium salt in the same fashion.

Procedure 4.
1-[3-(Trifluoromethyl)phenyl]-4-(3-chloropropyl)piperazine

To a solution of 7.36 g. (0.184 mole) of sodium hydroxide in 75 ml. of water and 75 ml. of acetone there is added 19.02 g. (0.074 mole) of 1-[3-(trifluoromethyl)phenyl]piperazine hydrochloride and 11.59 g. (0.074 mole) of 1-bromo-3-chloropropane, and the resulting mixture is stirred at 27° for 18 hrs. The organic layer is then separated and concentrated to an oil under reduced pressure. The oil is treated with hot (85°) 6 N HCl until solution is complete, and the resulting solution is filtered and stored at 5° for 18 hrs. The precipitate which forms is collected on a filter to afford 14.73 g. (66%) of the hydrochloride salt of the product, m.p. 190°–192°.

Procedure 5.
2-[3-[4-[3-(Trifluoromethyl)phenyl]-1-piperazinyl]-propyl]-1,2,4-triazolo[4,3-a]pyridin-3(2H)-one (MJ 12762)

The hydrochloride salt of 1-(3-chloropropyl)-4-[3-(trifluoromethyl)phenyl]piperazine, 6.41 g. (0.0187 mole) is dissolved in dilute KOH solution and the free base which is formed is extracted into ether. The ether solution is washed with water and brine, dried over magnesium sulfate, and concentrated under reduced pressure to afford the desired free base. A suspension of 2.61 g. (0.0166 mole) of the sodium salt of 1,2,4-triazolo[4,3-a]pyridin-3(2H)-one and 5.09 g (0.0166 mole) of 1-(3-chloropropyl)-4-[3-(trifluoromethyl)phenyl]piperazine in 100 ml. of acetonitrile is treated with approximately 50 mg. of potassium iodide, and refluxed for 24 hrs. The mixture is then cooled and filtered, and the filtrate concentrated to an oil under reduced pressure. The residual oil solidifies when triturated with ether. This solid is recrystallized twice from ethanol to give 4.34 g. (58%) of product, m.p. 207.5°–209.5°.

Anal. Calcd. for $C_{20}H_{22}F_3N_5O \cdot 1.25HCl$: C, 53.26; H, 5.20; N, 15.53. Found: C, 53.13; H, 5.10; N, 15.33.

NMR (DMSO-d$_6$): 2.35 (2,m), 3.44 (8,m), 4.07 (4,m), 6.73 (1,m), 7.35 (6,m), 7.44 (1,m).

IR: 710, 760, 1130, 1320, 1460, 1650, 1715, 2600, 2930 cm$^{-1}$.

By adaptation of Procedure 1 to various 2-chloro-3,4,5, or 6-lower alkyl substituted pyridine starting materials, and conversion of the resulting 5,6,7, or 8-lower alkyl-1,2,4-triazolo[4,3-a]pyridin-3(2H)-ones according to the processes of Procedures 3 and 5, various substituted homologs of the product of Procedure 5 may be prepared as follows.

| Pyridine Starting Material | Formula I 3-CF$_3$ |
|---|---|
| 2-Chloro-6-methylpyridine | $R^1$ = 5-CH$_3$ |
| 2-Chloro-6-ethylpyridine | $R^1$ = 5-CH$_2$CH$_3$ |
| 2-Chloro-6-(n-propyl)pyridine | $R^1$ = 5-(n-C$_3$H$_7$) |
| 2-Chloro-6-(tert.-butyl)pyridine | $R^1$ = 5-(tert.-butyl) |
| 2-Chloro-3-methylpyridine | $R^1$ = 8-CH$_3$ |
| 2-Chloro-4-methylpyridine | $R^1$ = 7-CH$_3$ |
| 2-Chloro-5-methylpyridine | $R^1$ = 6-CH$_3$ |

Similarly by substitution of 1-[2-(trifluoromethyl)phenyl]piperazine or 1-[4-(trifluoromethyl)phenyl]piperazine for 1-[3-(trifluoromethyl)phenyl]piperazine in Procedure 5, the corresponding 2-[3-[4-[2-, or 4-(trifluoromethyl)phenyl]-1-piperazinyl]propyl]-1,2,4-triazolo[4,3-a]pyridin-3(2H)-ones can be prepared.

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and compressed into tablets. The tablets may be used uncoated or coated by known techniques.

In the preparation of soft gelatin capsules comprised of a shell made of gelatin and glycerine or the like, the active ingredient is mixed with a vegetable oil and encapsulated in conventional manner. Hard gelatin capsules may contain granules of the active ingredient in combination with a solid, pulverulent carrier such as lactose, sucrose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A suitable injectible composition comprises an aqueous solution of a water soluble pharmaceutically acceptable salt adjusted to physiologically acceptable pH.

What is claimed is:

1. The 2-substituted triazolo[4,3-a]pyridin-3(2H)-ones having the formula

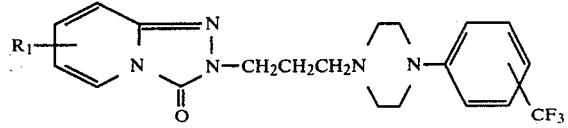

and the pharmaceutically acceptable acid addition salts thereof wherein $R^1$ is hydrogen or lower alkyl located in the 5, 6, 7, or 8 position of the 1,2,4-triazolo[4,3-a]pyridin-3(2H)-one ring and having 1 to 4 carbon atoms, and $CF_3$ is located in the 2, 3, or 4 position of the phenyl ring.

2. The compound of claim 1 wherein $R^1$ is lower alkyl.

3. The compound of claim 1 wherein $R^1$ is hydrogen.

4. The compound of claim 1, 2-[3-[4-[3-(trifluoromethyl)phenyl]-1-piperazinyl]propyl]-1,2,4,-triazolo[4,3-a]pyridin-3(2H)-one.

5. The compound of claim 1, 2-[3-[4-[3-(trifluoromethyl)phenyl]-1-piperazinyl]propyl]-1,2,4-triazolo[4,3-a]pyridin-3(2H)-one hydrochloride.

6. The process for exerting an antidepressant effect which comprises administering orally or parenterally to a patient suffering from either neurotic or endogenous depression a non-toxic antidepressively effective dose of a compound claimed in claim 1.

* * * * *